United States Patent [19]

Awazu et al.

[11] Patent Number: 5,213,839
[45] Date of Patent: May 25, 1993

[54] METHOD OF APPLYING SILICONE OIL TO INJECTION NEEDLE AND APPARATUS USED THEREFOR

[75] Inventors: Fumio Awazu, Otsu; Hideo Kuwabara, Kusatsu, both of Japan

[73] Assignee: Nissho Corporation, Osaka, Japan

[21] Appl. No.: 736,144

[22] Filed: Jul. 26, 1991

[30] Foreign Application Priority Data

Jul. 30, 1990 [JP] Japan .................................. 2-201759

[51] Int. Cl.$^5$ ........................................... B05D 1/18
[52] U.S. Cl. ..................................... 427/2; 427/289; 427/430.1; 427/435; 118/429
[58] Field of Search ................. 427/435, 2, 434.5, 282, 427/, 430.1, 289; 118/429

[56] References Cited

U.S. PATENT DOCUMENTS

| | | | |
|---|---|---|---|
| 1,452,635 | 4/1923 | Berninghaus | 427/435 |
| 2,262,045 | 11/1941 | Pollitt | 427/282 |
| 2,747,756 | 5/1956 | Hartop, Jr. et al. | 427/2 |
| 2,812,740 | 11/1957 | Kirijan | 118/425 |
| 2,814,296 | 11/1957 | Everett | 427/2 |
| 3,042,548 | 7/1962 | Aikens | 427/435 |
| 3,470,011 | 9/1969 | Szumski et al. | 427/2 |
| 3,942,408 | 3/1976 | Bernath | 427/435 |
| 4,153,739 | 5/1979 | Kessler | 427/2 |
| 4,308,232 | 12/1981 | Crouther et al. | 427/379 |
| 4,338,879 | 7/1982 | Makeev et al. | 427/435 |
| 4,430,358 | 2/1984 | Wada | 427/2 |
| 4,530,861 | 7/1985 | Sippel et al. | 427/282 |
| 4,720,521 | 1/1988 | Spielvogel et al. | 427/387 |
| 4,964,366 | 10/1990 | Kurokawa et al. | 118/429 |
| 4,997,359 | 3/1991 | Lebrun | 118/429 |

Primary Examiner—Michael Lusigan
Assistant Examiner—Diana Dudash
Attorney, Agent, or Firm—Armstrong, Westerman, Hattori, McLeland & Naughton

[57] ABSTRACT

A method for applying silicone oil to a back end of an injection needle having a hub with a center hole and a cannula inserting in the center hole, in which the cannula has a front end with a sharp bevel and a back end with another sharp bevel and the back end terminates within the hub. The method comprises allowing silicone-containing-liquid to continue to overflow at a constant rate of flow from a top end of a rising pipe having an inner diameter larger than an outer diameter of the cannula and an outer diameter smaller than an inner diameter of the hub, and concurrently dipping the back end into silicone-containing-liquid at the top end of the rising pipe. Silicone with no foreign matter can be applied to the injection needle while preventing adhesion of silicone containing liquid to the hub. The apparatus used for carrying out the method is also disclosed.

1 Claim, 4 Drawing Sheets

METHOD OF APPLYING SILICONE OIL TO INJECTION NEEDLE AND APPARATUS USED THEREFOR

BACKGROUND OF THE INVENTION

The present invention relates to a method and an apparatus for applying silicone oil (hereinafter referred to simply as silicone) to a back end of a injection needle comprising a hub and a cannula, in which the cannula has a front end projecting from the hub and a back end terminating within the hub.

Conventional injection needles include, as one type, the specific injection needle such as one called "insulin needle" available from Novo Nordisk A/S, which has a specific structure and configuration wherein a cannula having a front end with a sharp bevel and a back end with another sharp bevel inserts in a center hole of a hub in such a manner that the back end projecting inside the hub terminates within the hub (hereinafter, this type of injection needle is merely referred to as injection needle).

In the general manufacturing process of injection needles, a sharp bevel end of a cannula attached to a hub is dipped into a vessel containing a liquid in which silicone oil is diluted with a volatile solution (referred to simply as silicone-containing-liquid in this specification) to apply silicone to the cannula, in order to improve sliding property of the cannula thereby reducing penetration force of the injection needle. In the case of the injection needle mentioned above, however, the normal dipping application causes silicone-containing-liquid to adhere to the hub since the back end of the cannula terminates within the hub and does not project from the hub. Adhesion of silicone-containing-liquid to the hub is undesirable since such adhesion causes problems that silicone-containing-liquid becomes wasteful, and a jig in the next step is contaminated. It further causes problems that the hands of an operator are soiled, or due to slipping of the hands attachment operation becomes difficult, since the hub is such a portion that is held by the hands when attaching an injection needle to a syringe.

Hitherto, application of silicone to the back end of the cannula has been carried out, for example, by a method wherein porous resin having a size smaller than the inner diameter of the hub is impregnated with silicone-containing-liquid, and the back end is pricked into the porous resin.

In the method using resin impregnated with silicone-containing-liquid, however, there are several drawbacks that (1) the application of silicone oil becomes difficult because the diluent in the silicone-containing-liquid evaporates and the composition of silicone-containing-liquid changes such that viscosity of the silicone-containing-liquid becomes too high, (2) contaminant, which is transferred from the cannula to the resin, is liable to adhere to the cannula again, (3) very small pieces of the resin are liable to adhere to the cannula, and the like.

The present invention was made in view of the drawbacks of the conventional method and apparatus for applying silicone to a back end of a injection needle, and an object of the present invention is to provide a method and an apparatus wherein composition of silicone containing liquid does not change substantially, and foreign matter does not adhere to the cannula.

SUMMARY OF THE INVENTION

In accordance with the present invention, there is provided a method of applying silicone oil to a back end of an injection needle having a hub with a center hole and a cannula inserted in the center hole, the cannula having a front end with a sharp bevel and a back end with another sharp bevel, the back end terminating within the hub, comprising:
 (a) allowing silicone-containing-liquid to continue to overflow from a top end of a rising pipe having an inner diameter larger than an outer diameter of the cannula and an outer diameter smaller than an inner diameter of the hub; and
 (b) concurrently dipping the back end of the cannula into silicone-containing-liquid at the top end of the rising pipe.

In the above-mentioned method, after the back end of the cannula is dipped into silicone-containing-liquid, air might be supplied from the front end into the cannula in which silicone-containing-liquid remains so as to blow the remaining liquid out of the back end.

In accordance with the present invention, there is also provided an apparatus of applying silicone oil to a back end of an injection needle, comprising:
 (a) a handling unit for handling an injection needle having a hub with a center hole and a cannula inserted in the center hole, the cannula having a front end with a sharp bevel and a back end with another sharp bevel, the back end terminating within the hub, with only contacting the hub of the injection needle;
 (b) a vertically rising pipe having an inner diameter larger than an outer diameter of the cannula and an outer diameter smaller than an inner diameter of the hub, and having a top open end formed in plane; and
 (c) a supplying portion of silicone-containing-liquid connected to a lower portion of the rising pipe for supplying silicone-containing-liquid at a constant rate of flow.

Thus, in the method and apparatus of the present invention, since silicone-containing-liquid is overflown at a constant rate of flow and the flow of silicone-containing-liquid has a diameter smaller than an inner diameter of the hub, and since the back end of the cannula is dipped into the flow of silicone-containing-liquid, without adhering silicone-containing-liquid to the inner surface of the hub, silicone oil is coated on the back end by silicone-containing-liquid which is flowing. Further, adhesion of foreign matter to the cannula is prevented, and substantial increase of viscocity of silicone-containing-liquid is not caused so that application of silicone can be carried out with silicone-containing-liquid always having a predetermined composition, since silicone-containing-liquid is renewed by flowing.

DETAILED DESCRIPTION

Embodiments of the invention will now be described by way of example only, in conjunction with the attached drawings.

Figure 1:
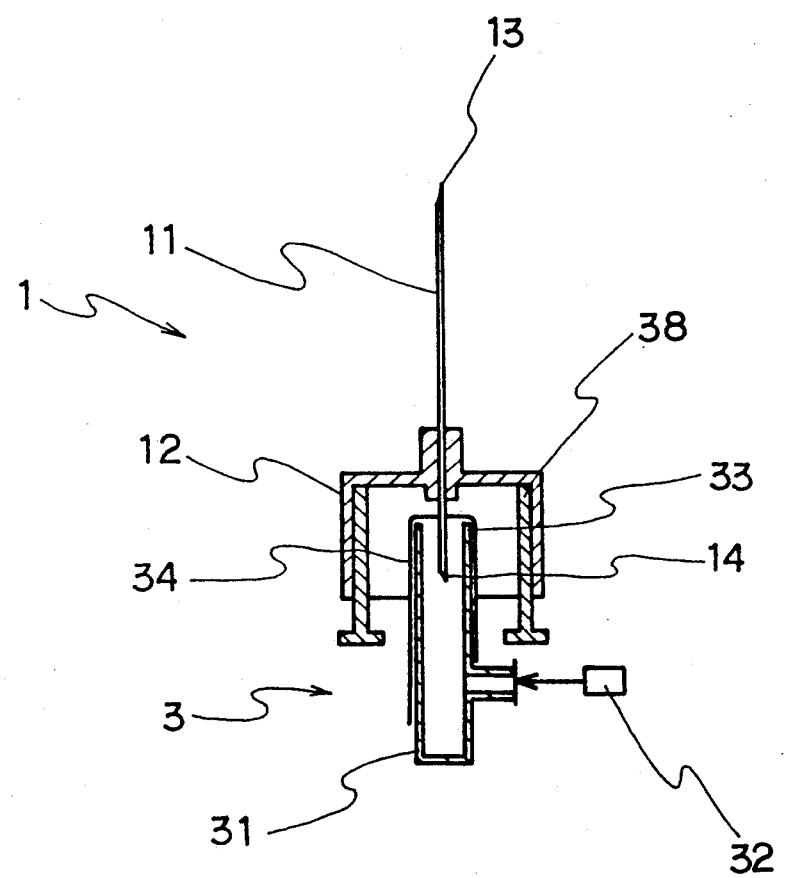
FIG. 1 is a sectional view of an embodiment of an apparatus of the present invention.

A silicone-applying apparatus 3 shown in FIG. 1 comprises
- a vertically rising pipe 31 having an inner diameter larger than an outer diameter of a cannula 13 and an outer diameter smaller than an inner diameter of a hub 12, and having a top open end 33 formed in plane, and
- a supplying portion of silicone-containing-liquid 32 connected to a lower portion of the rising pipe 31 for supplying silicone-containing-liquid at a constant rate of flow.

In the apparatus of FIG. 1, there is also provided an outer tube 38 supporting the hub 12 and surely preventing adhesion of silicone-containing-liquid to the hub 12. The outer tube 38 has an outer diameter smaller than the inner diameter of the hub 12 and an inner diameter larger than the outer diameter of the rising pipe 31, and has a top end higher than that of the rising pipe 31.

The injection needle 1, to which silicone is applied, is an injection needle wherein a cannula 11 having sharp bevels at both a front end 13 and a back end 14 is inserted into a center hole of a hub 12, and the back end 14 projecting inside the hub 12 terminates within the hub 12.

Thus, in the method of the present invention, silicone-containing-liquid is overflown at a constant rate of flow from an uppermost end or top open end of the rising pipe 31 having an inner diameter larger than an outer diameter of the cannula 11 and having an outer diameter smaller than an inner diameter of the hub 12. Silicone is coated on the back end 14 of the injection needle 1 by dipping the back end 14 into silicone-containing-liquid at the uppermost end of the rising pipe 31.

The above-mentioned dipping is carried out by the handling unit which handles the injection needle 1 by only contacting hub 12 of the injection needle 1.

In the preferred embodiment, about 20 to 50 injection needles 1 are arranged in a row and handled, so that silicone-coating to back ends 14 is carried out at one time. In this case, there are provided rising pipes 31 whose number corresponds to that of arranged injection needles 1.

Silicone-containing-liquid is supplied from a supplying portion of silicone-containing-liquid (not shown) to a lower portion of the rising pipe 31 at a constant rate of flow. As a supplying portion of silicone-containing-liquid, fixed delivery pumps such as plunger pumps and diaphragm pumps can be used. However, usable pumps are not limited thereto in the present invention.

The supply of silicone-containing-liquid of 10 to 30 ml/min is enough for one rising pipe in the case of, for example, a rising pipe 31 of which uppermost opening has an inner diameter of 4 mm and an outer diameter of 5 mm (the intermediate portion of the vertical riser pipe is thinned to 3 mm). In general the supply amount of about 20 ml/min is employed. Flow velocity of this supply amount is 1.33 to 3.98 cm/sec on the basis of an inner diameter of the above rising pipe.

When the supply of silicone-containing-liquid is too small, renewal of silicone-containing-liquid becomes insufficient. On the other hand, when it is too large, there is a danger that silicone-containing-liquid adheres to the inner surface of the hub on overflowing silicone-containing-liquid.

When a large number of injection needles 1 are coated with silicone at one time as stated above, silicone-containing-liquid can be supplied, for example, to all rising pipes 31 from one supplying unit of silicone-containing-liquid.

Viscosity of the above-mentioned silicone-containing-liquid is preferably from about 20 to 100 cP. When viscosity is too low, coating of silicone becomes insufficient. On the other hand, when viscosity is too high, coating of silicone becomes difficult and finally silicone in particle condition adheres to the cannula.

In the method and apparatus of applying silicone to the back end 14, it is possible to recover overflown silicone-containing-liquid while coating the back end 14 with silicone oil and to recycle the recovered silicone-containing-liquid after adjustment of composition, adjustment of viscosity removal of impurities and the like are carried out as necessary.

Thus, in the method and apparatus of the present invention, silicone-containing-liquid is overflown with formation a certain adequate shape enabling the dipping of the back end 14 without contacting the inner surface of the hub. Accordingly, silicone is sufficiently coated on the back end 14 with silicone-containing-liquid of which composition, viscosity and the like are always kept in an adequate condition and which does not contain impurities, so that shortage of silicone or adhesion of foreign matter is not caused. Further, adhesion of silicone-containing-liquid to the inner surface of the hub is certainly avoided.

Figure 2:
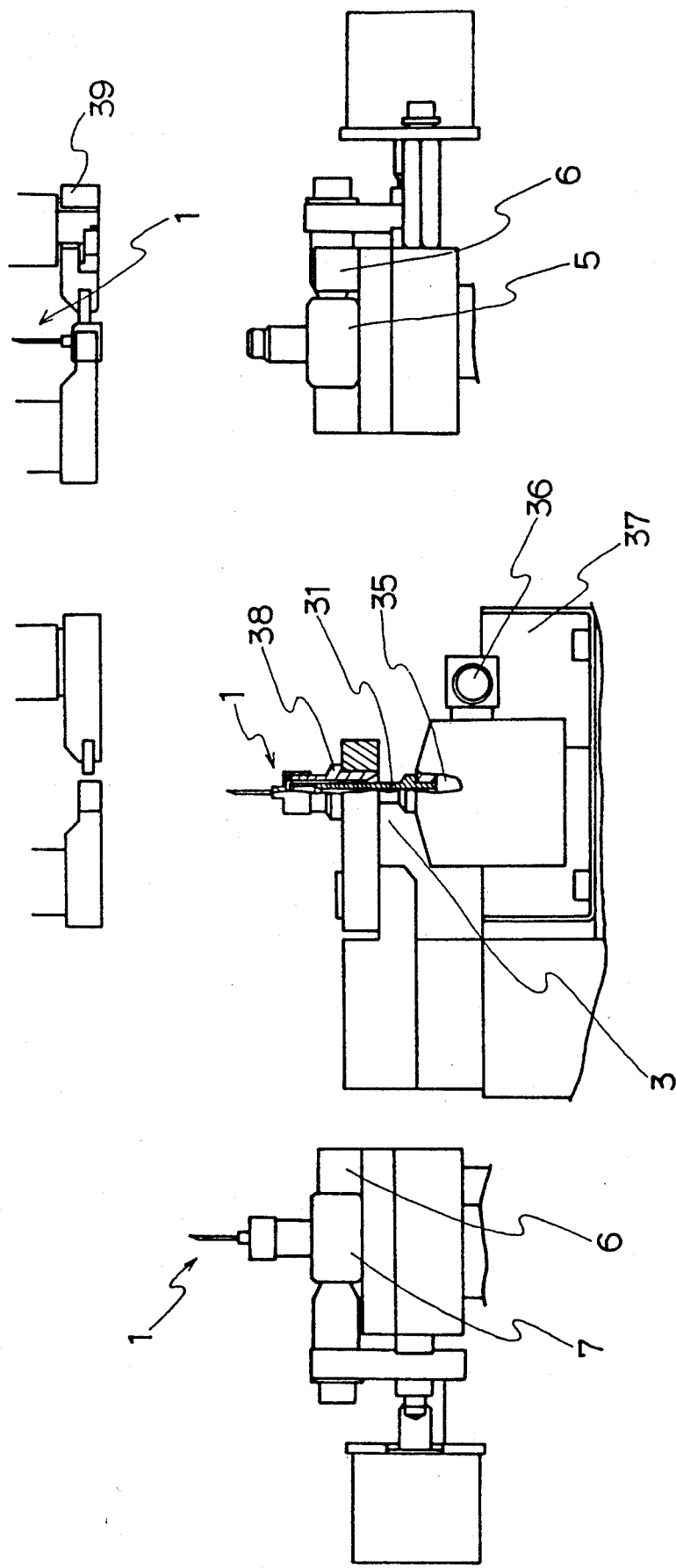
FIG. 2 is a side view showing a layout of the apparatus of the present invention.

FIG. 2 shows an example of a step of silicone-coating to a back end of a cannula during transference of a subassembly jig. In FIG. 2, an injection needle 1 is transferred from a first subassembly jig 5 conveyed on a conveyor line 6 shown on the right of FIG. 2 to a silicone-applying apparatus 3 shown on the center of FIG. 2. After silicone-coating is carried out, the injection needle 1 is transferred to a second subassembly jig 7 on a conveyor line 6 shown on the left of FIG. 2.

The transference of the injection needle 1 is carried out by a handling unit 39 which handles the injection needle 1 by only contacting the hub of the injection needle 1.

The silicone-applying apparatus 3 has a chamber of silicone-containing-liquid 35 for connecting a vertically rising pipe 31 and a supplying portion of silicone-containing-liquid (not shown), and a connecting pipe 36. The apparatus 3 further has a vessel 37 for collecting silicone-containing-liquid overflown from the top of the rising pipe 31, and an outer tube 38 supporting a hub thereby preventing adhesion of silicone-containing-liquid to the hub.

Figure 3:
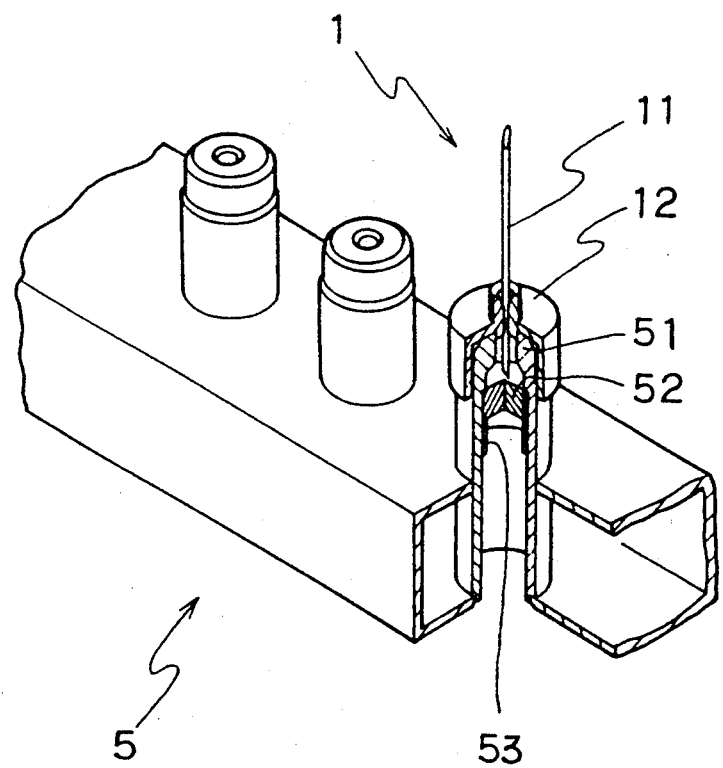
FIG. 3 is a partially-cut-off perspective view of a first subassembly jig.

The first subassembly jig 5 is, as shown in FIG. 3, so designed that plural injection needles 1 are mounted in a row, with the cannula 11 being inserted into the center hole of the hub 12, and with the front end pointed upward.

The number of the injection needles 1 mounted on one first subassembly jig 5 is such number of injection needles that are coated with silicone at one time. In order to make readily understandable, some omissions and cuttings away are used appropriately in FIG. 3.

As shown in section in FIG. 3, the first subassembly jig 5 has a hub-supporting portion 51, a cannula-supporting portion 52, and a fixing spring 53 which may be a ring-shaped spring. These components are so designed and arranged that the predetermined inserting depth of the cannula is equal to a depth when the hub 12 is put on the hub-supporting portion 51 and the back end (the lower end) of the cannula 11 abuts the cannula-supporting portion 52.

That is in the upstream steps, the cannula 11 and the hub 12 are connected to each other to form a hub-cannula assembly by using the above specific structure of the first subassembly jig 5, and then the assembly is transferred to near the silicone-applying apparatus 3 along the conveyor line 6.

Figure 4:
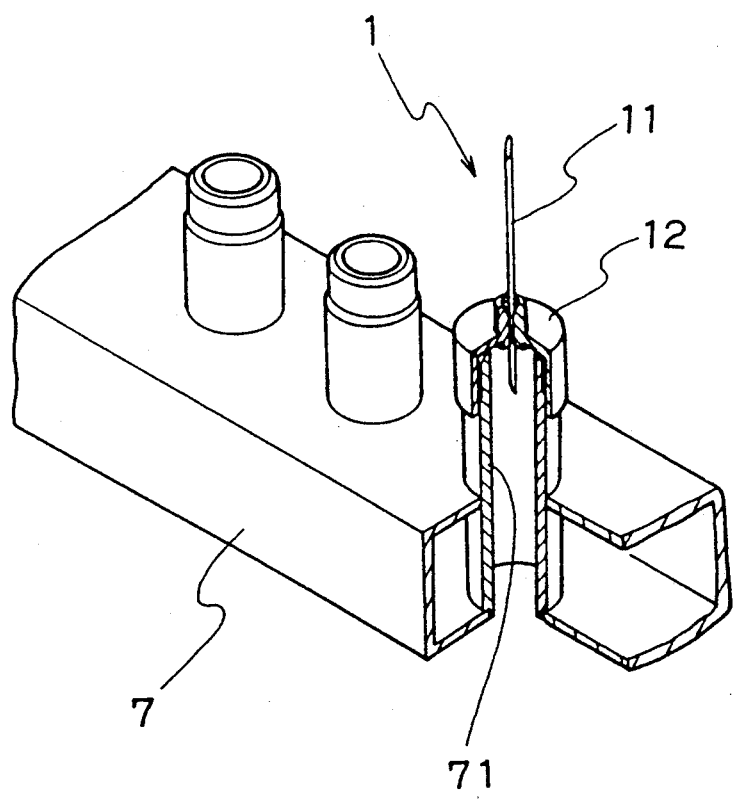
FIG. 4 is a partially-cut-off perspective view of a second subassembly jig.

On the other hand, as shown in FIG. 4, the second subassembly jig 7 is to support the hub 12 of the injection needle 1 with the front end of the cannula 11 pointed upward.

One second subassembly jig 7 can carry the same number of the injection needles 1 as one first subassembly jig 5.

As shown in section in FIG. 4, the second temporary support 7 has a hub-supporting portion (a hollow cylindrical rest) 71 having internally a relatively large penetrating bore.

By transferring the assembly to the jig having the above-mentioned structure, it becomes easy in the next step to pass air from the front end 13 through the cannula 11 to blow the remaining silicone-containing-liquid out of the cannula.

The method and apparatus of the present invention facilitate advanced automatization. For example, by employing a layout shown in FIG. 2, the apparatus can be arranged between a step for connecting a cannula and a hub as a former step and a step for removing remaining-silicone-containing liquid or an inspection step as a latter step without reducing efficiency of total steps.

According to the method and apparatus of the present invention, silicone with no foreign matter can be sufficiently applied to the above-mentioned injection needle while preventing adhesion of silicone-containing-liquid to the hub, and advanced automatization is facilitated.

What is claimed is:

1. A method of applying silicone oil to a back end of an injection needle including a hub having a center hole and a cap and a cannula inserted in the center hole, the cannula having a front end with a sharp bevel and a back end with another sharp bevel, the back end terminating within the cap of the hub, comprising:
   (a) allowing silicone-containing-liquid to continuously overflow from a top end of a rising pipe having an inner diameter larger than an outer diameter of the cannula and an outer diameter smaller than an inner diameter of the hub, and
   (b) concurrently dipping the back end of the cannula into silicone-containing-liquid at the top end of the rising pipe without contacting the hub with the silicone-containing-liquid.

* * * * *